United States Patent [19]

Hiruta

[11] Patent Number: 5,658,265

[45] Date of Patent: Aug. 19, 1997

[54] ADAPTOR FOR CONNECTING TUBES TO AN ANIMAL

[75] Inventor: Masahiro Hiruta, Ibaraki, Japan

[73] Assignee: Tsumura & Co., Tokyo, Japan

[21] Appl. No.: 490,867

[22] Filed: Jun. 15, 1995

[30] Foreign Application Priority Data

Jun. 24, 1994 [JP] Japan .................................. 6-143206

[51] Int. Cl.⁶ .................................................. A61M 25/00
[52] U.S. Cl. .............................. 604/283; 604/280; 604/174
[58] Field of Search .................................. 604/283, 280, 604/174

[56] References Cited

U.S. PATENT DOCUMENTS

| | | | |
|---|---|---|---|
| 4,254,773 | 3/1981 | Waldbillig | 604/283 |
| 5,167,647 | 12/1992 | Wijkamp et al. | 604/283 |
| 5,171,216 | 12/1992 | Dasse et al. | 604/283 |

*Primary Examiner*—Robert A. Hafer
*Assistant Examiner*—Benjamin Koo
*Attorney, Agent, or Firm*—Kanesaka & Takeuchi

[57] ABSTRACT

Coaxial infusion pipes are disposed in a fixed shaft body and the ends of the pipes pass into a rotary shaft body. The fixed shaft body and the rotary shaft body are rotatably joined by bearings. Packings are provided inside the rotary shaft body in correspondence with the pipes. Only lip portions of the packings are in sliding contact with the pipes. The sliding resistance between the infusion pipes and the packings as seal members is low, and the rotary shaft body can rotate extremely lightly and with high precision.

7 Claims, 7 Drawing Sheets

Prior Art

Fig. 8

Prior Art

ADAPTOR FOR CONNECTING TUBES TO AN ANIMAL

FIELD OF THE INVENTION AND RELATED ART STATEMENT

This invention relates to an adaptor used for infusions to animals, and particularly to an adaptor suitable for giving infusions to a small animal such as a mouse or a rat. More specifically, the invention relates to an animal infusion tube adaptor which is disposed midway along infusion tubes to prevent the tubes from twisting.

In order to administer medical fluids continuously for a fixed period of time to a test animal in a rearing cage, as an infusion adaptor, for a large animal such as a dog, a rabbit, a cat or a pig, a jacket is put on the animal and infusion tubes are connected to the animal by way of a rotary adaptor fitted to this jacket.

For small animals such as mice and rats, small and light adaptors are used. Such a small and light adaptor is disclosed in Japanese Utility Model Publication No. H.5-63522 (Application No. H.4-5863).

The adaptor disclosed in Japanese Utility Model Publication No. H.5-63522 will now be described with reference to the accompanying drawings.

Figure 7:
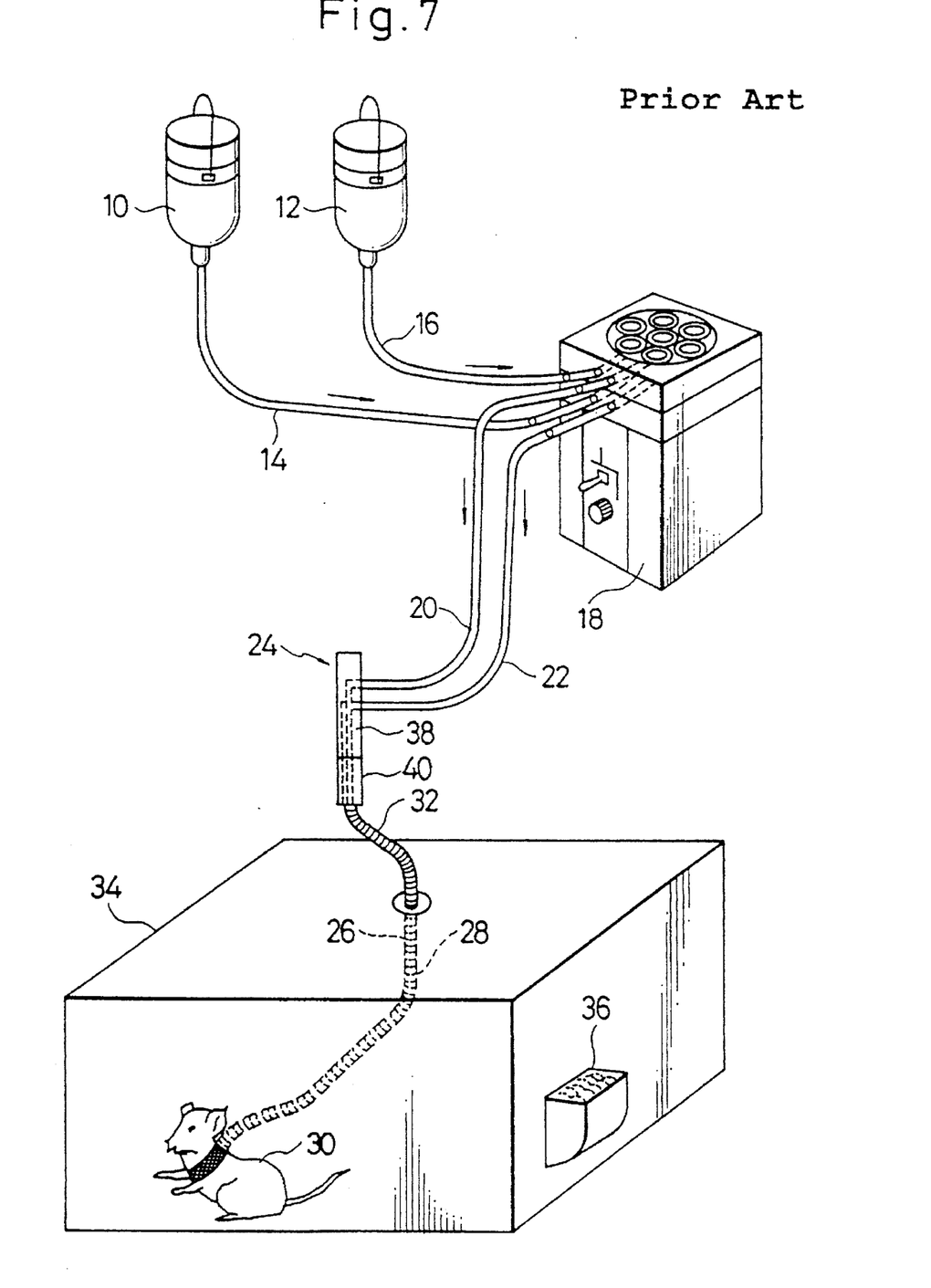
FIG. 7 is a perspective view showing a conventional adaptor in use.
Figure 8:
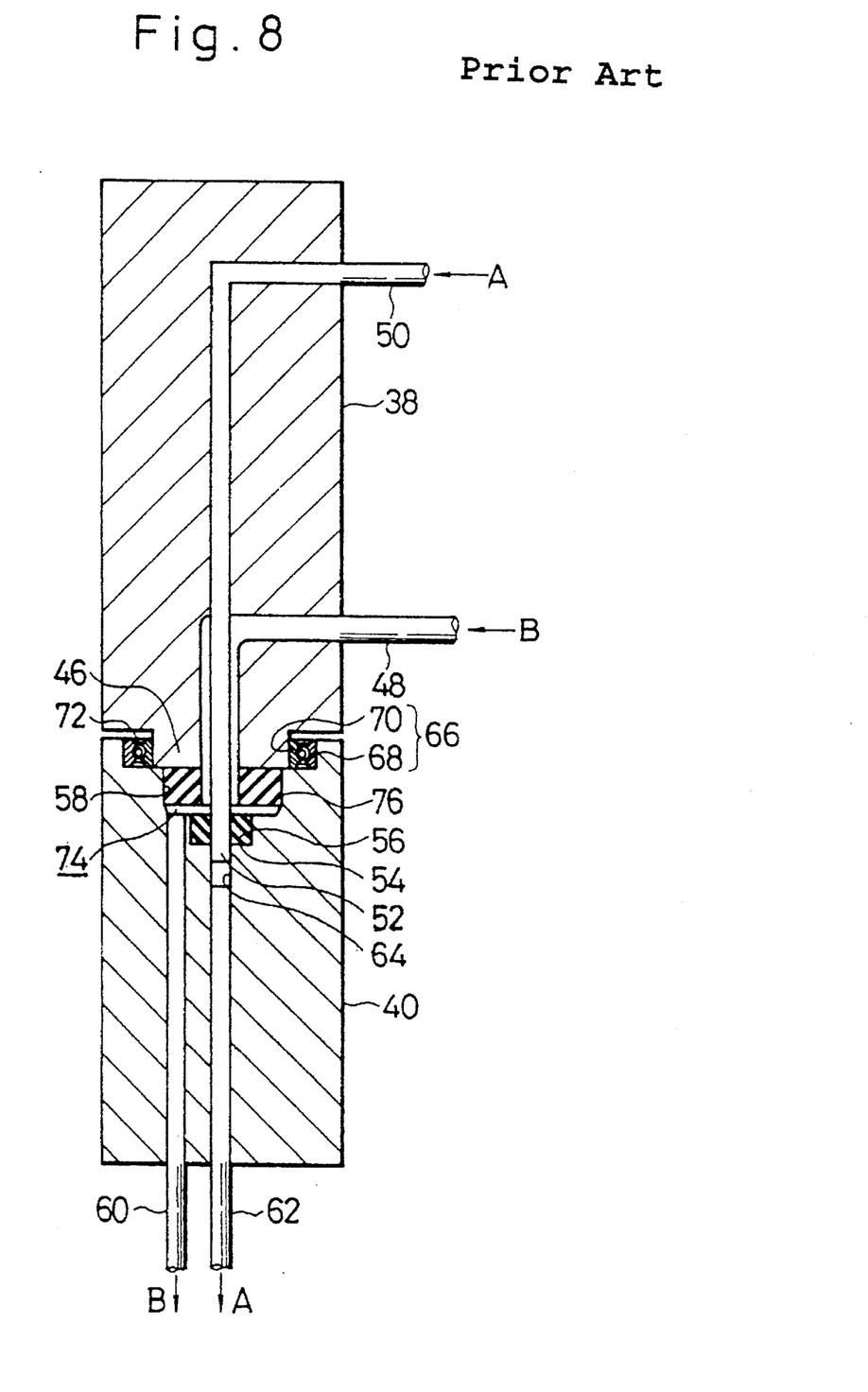
FIG. 8 is a sectional view of a conventional adaptor.

FIG. 7 is a schematic perspective view showing continuous infusion to a small test animal (a rat) using an animal infusion tube adaptor according to the above-mentioned publication, and FIG. 8 is a sectional view of the same adaptor.

Referring to FIG. 7, liquids in infusion bottles 10 and 12 are fed to a microtube pump 18 through tubes 14 and 16 and then from the microtube pump 18 through tubes 20 and 22 to an adaptor 24. Two tubes 26 and 28 lead out of this adaptor 24, and two liquids are infused to a rat 30. The tubes 26 and 28 are covered by a protective coil 32. The rat 30 is kept in a cage 34, and food 36 is placed in the cage 34.

As shown in FIG. 8, this adaptor 24 is made up of a rotary shaft body 40 rotatably joined to a fixed shaft body 38.

The fixed shaft body 38 as a whole is shaped like a cylindrical bar, and a cylindrical projection 46 is provided at a front end thereof. Two pipes 48 and 50 are embedded in the fixed shaft body 38 and are lead through the front end surface of this projection 46 to outside the fixed shaft body 38. The rear ends of these pipes 48 and 50 extend out of the side surface of the fixed shaft body 38 in a direction perpendicular to the axial centerline thereof.

The insides of these pipes 48 and 50 are fluid passages. The front ends of the pipes 48 and 50 are coaxial, and these front ends of the pipes 48 and 50 project from the central portion of the front end surface of the projection 46 in the axial direction. The front end of the pipe 50 projects further forward than the front end of the pipe 48 and constitutes a thin or narrow pipe 52 inserted into the rotary shaft body 40 which will be further discussed later.

The pipes 48 and 50 are made of metal and the rest of the fixed shaft body 38 is made of synthetic resin; the pipes 48 and 50 are embedded in the synthetic resin by insert molding or the like.

The rotary shaft body 40 is substantially cylindrical, and a two-level cylindrical recess 58 is provided in a front end thereof. A packing receiving hole 54 is provided in the central portion of the bottom of the recess 58, and a first packing 56 consisting of silicon rubber or fluoro rubber is closely inserted in this packing receiving hole 54. Two pipes 60 and 62 are embedded in the rotary shaft body 40 and connect the inside of the recess 58 to the end surface of the rotary shaft body 40 at the bottom of the drawing. These pipes 60 and 62 are made of metal and are embedded in the synthetic resin constituting the rest of the rotary shaft body 40 by insert molding or the like.

The pipe 60 is disposed in a position in the rotary shaft body 40 not on the axial centerline thereof. The pipe 62 is disposed on the axial centerline of the rotary shaft body 40 and extends from the rotary shaft body 40 to the rear end surface (the bottom end surface in the drawing) thereof and projects beyond this rear end surface. The upper end of the pipe 62 in the drawing is connected to the bottom of the packing receiving hole 54 by way of a small hole 64 provided in the rotary shaft body 40. As a result, a liquid passage is formed by the insides of the pipes 60 and 62 and the small hole 64.

The outer ring 68 of a ball bearing 66 (in this preferred embodiment a shield type bearing) is fixed to the inner surface of the wider part of the recess 58. This ball bearing 66 has the outer ring 68, an inner ring 70 and balls 72, and the outer ring 68 is fixed to the rotary shaft body 40. The inner ring 70 is fitted and adhered to the projection 46 of the fixed shaft body 38.

A ringlike second packing 76 is inserted between the end surface of the projection 46 and the bottom of the recess 58, and a gap 74 is formed between this second packing 76 and the bottom of the recess 58. When this projection 46 is inserted into the recess 58, the end of the pipe 48 fits watertightly in the inner hole of the second packing 76. The thin pipe 52 constituting the end of the pipe 50 is thrust through the soft rubber packing 56, and the end of this thin pipe 52 is inserted into the small hole 64.

Because the thin pipe 52 is thrust through the soft rubber packing 56 in this way, the contact between the outer surface of the thin pipe 52 and the packing 56 is extremely good, and the watertightness of this part is good. As a result, there is no leakage of liquid between the gap 74 and the small hole 64. The gap 74 and the ball bearing 66 are also sealed from each other by the packing 76, and there is no leakage between the two.

In the rotary adaptor of FIG. 7 and FIG. 8 constituted in this way, liquid fed down through the pipe 50 passes through the thin pipe 52 and the pipe 62 and is fed out as shown by the arrows A in the drawings. Liquid fed down through the pipe 48 first flows from the pipe 48 into the gap 74 and is then sent out through the pipe 60 as shown by the arrows B.

In the animal infusion tube adaptor of Japanese Utility Model Publication No. H.5-63522, because the contact area between the packings 56 and 76 and the pipes 50 and 48 is large, along with rotation of the rotary shaft body 40 a large frictional force is generated between the packings 56 and 76 and the pipes 50 and 48, and the rotation is rather heavy.

Because the inner and outer surfaces of the packings 56 and 76 are simple cylindrical surfaces, when liquid pressure acts on the packings, the packings deform and the contact area between the packings 56 and 76 and the pipes 50 and 48 decreases. Therefore, the sealing effect of the packings is impaired and leakage of liquid from the adaptor and mixing of liquids in the adaptor occur.

When in order to improve the seal between the packings and the pipes the packings are made to contact the pipes more strongly, the rotation of the rotary shaft body becomes heavy. Reversely, when the contact between the packings and the pipes is kept weak to make the rotation light, the sealing effect is also reduced.

OBJECT AND SUMMARY OF THE INVENTION

An object of the invention is to provide an adaptor in which the rotary body rotates extremely lightly and also there is absolutely no leakage of liquid.

An animal infusion tube adaptor according to the invention is an adaptor disposed midway along a plurality of tubes running between an animal and equipment, and comprises: a fixed shaft body to which equipment side tubes are connected; a rotary shaft body to which animal side tubes are connected; a cylindrical projection provided at one end of one of the shaft bodies; a first cylindrical recess provided in the other shaft body into which the projection is inserted, the projection and the first recess being coaxially rotatably joined by a plurality of coaxially disposed annular bearings; coaxial pipes extending from a central portion of an end surface of one of the shaft bodies, the pipes extending further from the end surface such that as the pipe is located inwardly, the pipe extends downwardly; a second cylindrical recess provided in a central portion of an end surface of the other shaft body for receiving the coaxial pipes; ringlike-seal members fitted around the pipes dividing the second recess in the shaft centerline direction into a plurality of chambers, each seal member making contact with the outer surface of a pipe and the inner surface of the second recess, one seal member making contact with each pipe, one chamber thereby being connected to the inside of one pipe only; liquid passages in the plurality of chambers severally connecting the chambers to outside the shaft bodies; and a lip portion provided around the inner edge of each seal member, the lip portion being urged into contact with the pipe around which the seal member is fitted by liquid pressure applied from the pipe.

Preferably, the lip portions are cylindrical.

Preferably, the inner surface of the lip portion which abuts with the outer surface of the pipe is tapered so that its diameter gradually decreases along one direction of the pipe axial centerline, and the lip portion has such flexibility that it can be so deformed by liquid pressure acting in said direction of the pipe axial centerline that the whole of the inner surface of the lip portion makes contact with the outer surface of the pipe.

In an adaptor according to the invention, twisting of the tubes is prevented by the rotary shaft body rotating with respect to the fixed shaft body coaxially about the axial centerline of the shaft bodies.

In this adaptor, a multiple pipe provided on the shaft center of either the rotary shaft body or the fixed shaft body is inserted into a second recess provided in the shaft center part of the other shaft body, and liquid passes through this multiple pipe from the fixed shaft body into a plurality of liquid passages on the rotary shaft body side and is infused to the animal.

In this adaptor, because the rotary shaft body is supported on the fixed shaft body by way of bearings, the rotary shaft body rotates extremely lightly.

In this adaptor, the seal members are provided with lip portions and liquid pressure applied from the pipes around which the seal members are fitted urges the seal members to make contact with the pipes and the watertightness of the sealing is thereby secured.

The inner surfaces of the lip portions are pressed into contact with the outer surfaces of the pipes by liquid pressure acting centripetally on the outer surfaces of the cylindrical lip portions.

Liquid pressure acting on the lip portions in the pipe axial direction causes the lip portions to deform so that tapered inner surfaces of the lip portions become untapered cylindrical inner surfaces. As a result, the lip inner surfaces make contact with the pipe outer surfaces over a wide area.

DETAILED DESCRIPTION OF THE PREFERRED EMBODIMENTS

Figure 1:
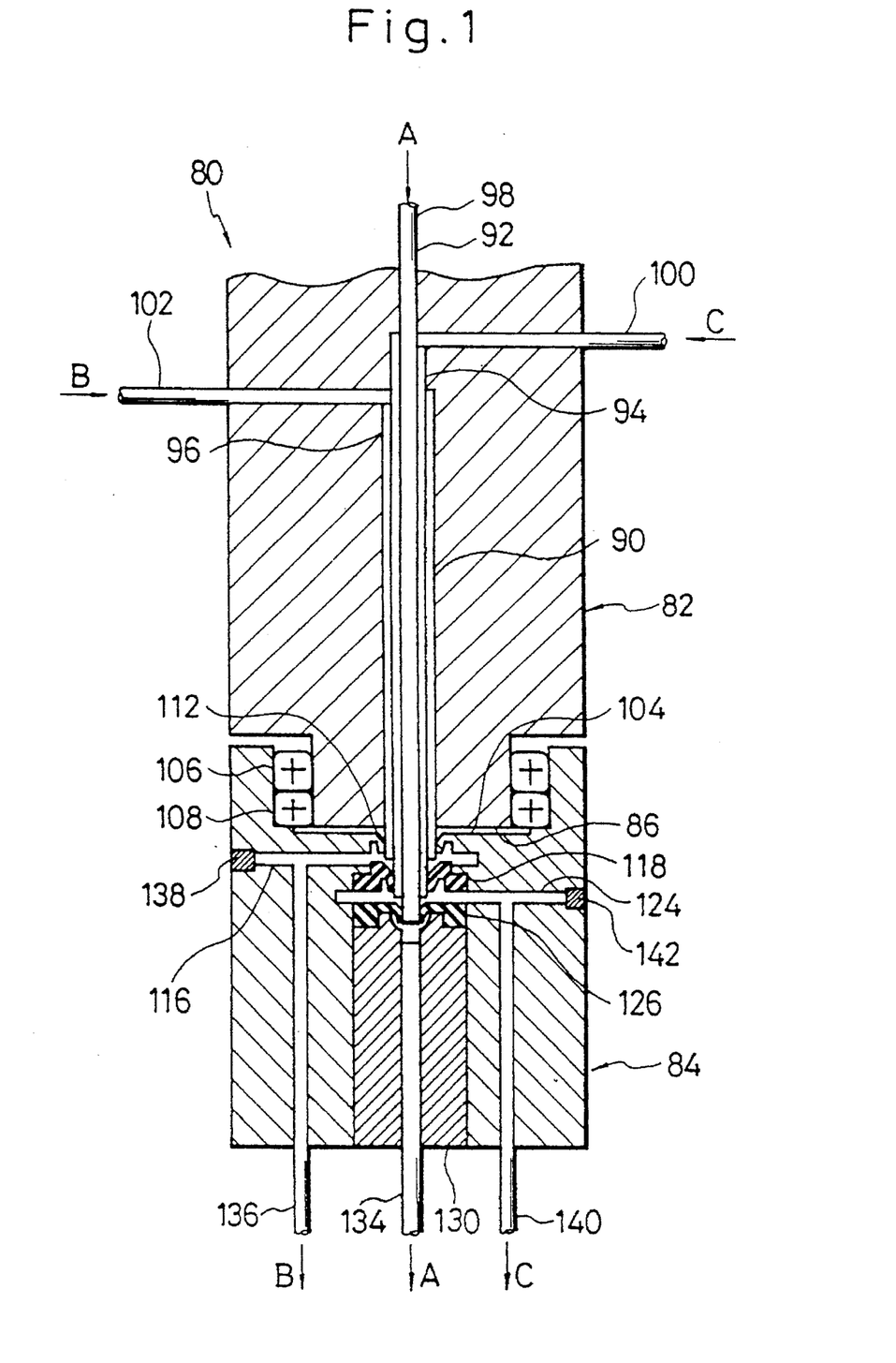
FIG. 1 is a sectional view of an animal infusion tube adaptor according to a first preferred embodiment of the invention.
Figure 2:
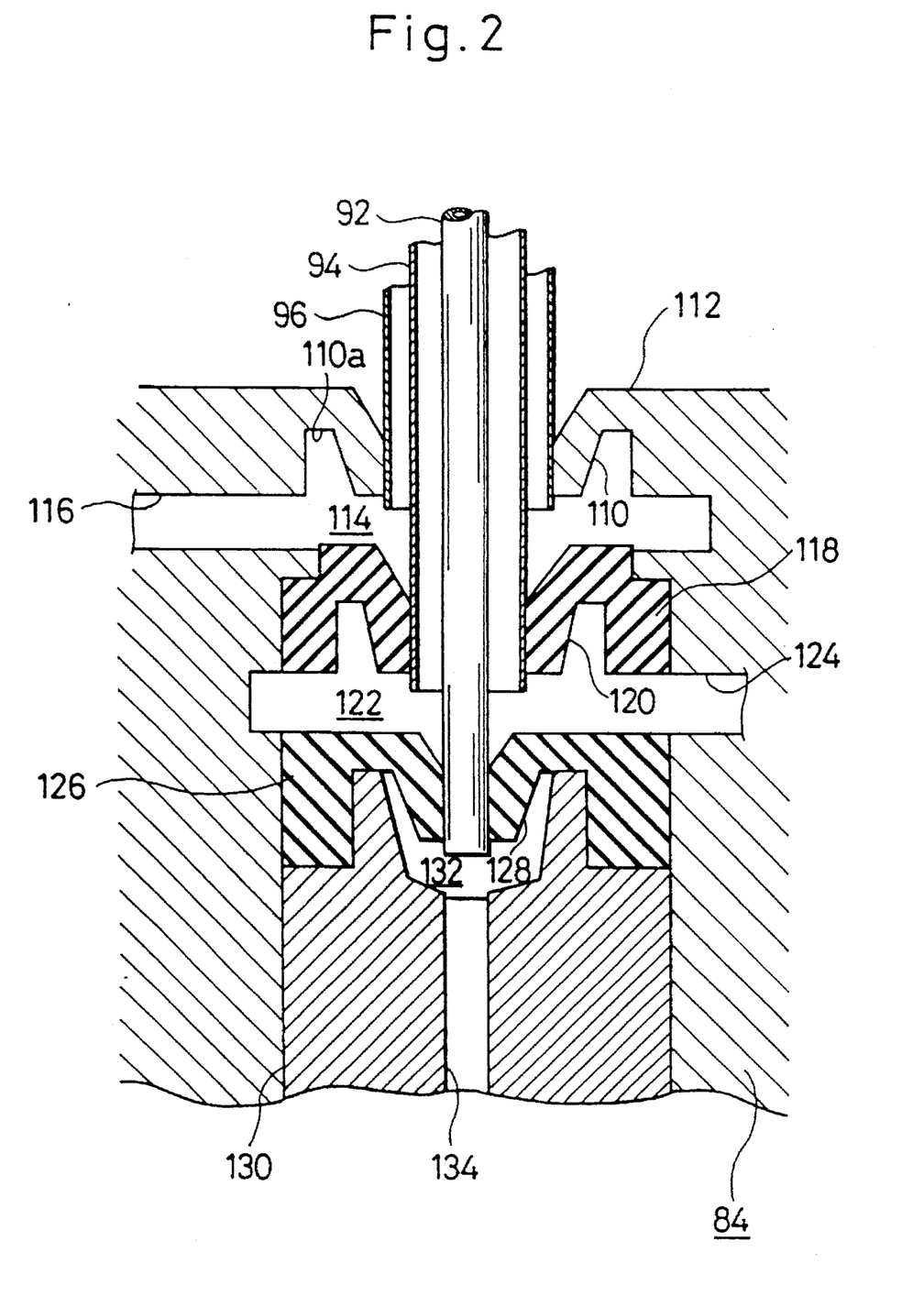
FIG. 2 is an enlarged detail view of the adaptor shown in FIG. 1.

Preferred embodiment of the invention will now be described with reference to the accompanying drawings. FIG. 1 is a sectional view of an animal infusion tube adaptor according to a first preferred embodiment of the invention, and FIG. 2 is an enlarged detail view of the adaptor shown in FIG. 1.

As shown in FIG. 1, this adaptor 80 is made up of a rotary shaft body 84 rotatably joined to a fixed shaft body 82.

In this first preferred embodiment, the fixed shaft body 82 as a whole is cylindrical and has a cylindrical projection 86 provided at its end. A multiple pipe 90 is embedded in the fixed shaft body 82 on the axial centerline thereof and runs from the end of the projection 86 to outside the fixed shaft body 82.

The pipe 90 is a triple pipe consisting of, from the inside to outside a first pipe 92, a second pipe 94 and a third pipe 96 combined coaxially. At the rear end of this pipe 90, the first pipe 92 extends out of the rear of the fixed shaft body 82 on the centerline thereof as an infusion tube 98. Inside the fixed shaft body 82, the second pipe 94 is connected to an infusion tube 100 extending perpendicular to the axial centerline of the fixed shaft body 82. The third pipe 96 also is connected inside the fixed shaft body 82 to an infusion tube 102 extending perpendicular to the centerline of the fixed shaft body 82. The infusion tube 100 and the infusion tube 102 extend away from each other and extend through the side of the fixed shaft body 82 to the outside.

The end of this pipe 90 projects forward beyond the end surface of the projection 86 of the fixed shaft body 82 (downward in FIG. 1) and into the rotary shaft body 84 which will be further discussed later. In this triple pipe 90, the first pipe 92 projects the farthest beyond the end surface of the projection 86, followed by the second pipe 94 and then the third pipe 96.

In this fixed shaft body 82, the fixed shaft body 82 is made of synthetic resin. The pipe 90 is made of metal and is embedded inside the fixed shaft body 82 by insert molding or the like.

The rotary shaft body 84 is substantially cylindrical, and a cylindrical recess 104 is provided in the end surface (the upper end in FIG. 1) of the rotary shaft body 84. Bearings 106 and 108 are fitted in the recess 104 along the axial centerline of the rotary shaft body 84. The outer peripheries of the outer rings of the bearings 106 and 108 are both fixed to the inner circumferential surface of the recess 104, and the inner peripheries of the inner rings are both fixed to the outer peripheral surface of the projection 86 of the fixed shaft body 82.

An opening of the diameter slightly smaller than the outer diameter of the third pipe 96 of the pipe 90 embedded in the fixed shaft body 82 is provided in the center of the bottom of the recess 104. A packing 112 is provided around the upper edge of this hole, and the central portion of this packing 112 forms a lip portion 110 which makes contact with the outer surface of the third pipe 96.

The packing 112 having this lip portion 110 is integral with the rotary shaft body 84. The lip portion 110 is substantially cylindrical and is so provided that it contracts centripetally and its diameter decreases when a liquid pressure is applied to its outer peripheral surface.

A chamber 114 is provided below the packing 112. A transverse infusion tube 116 is provided in the inner side surface of the chamber 114, the opening at the end of the third pipe 96 is positioned inside the chamber 114, and the third pipe 96 and the transverse infusion tube 116 are connected by the chamber 114.

A packing 118 is disposed below the chamber 114, and the lower surface of the chamber 114 is formed by the upper surface of the packing 118. Like the packing 112, the packing 118 has a substantially cylindrical lip portion 120. This lip portion 120 is in contact with the outer surface of the second pipe 94.

A chamber 122 is provided below the packing 118. A transverse infusion tube 124 is provided in the inner side surface of the chamber 122, the opening at the end of the second pipe 94 is positioned inside the chamber 122, and the second pipe 94 and the transverse infusion tube 124 are connected by the chamber 122.

A packing 126 is disposed below the chamber 122, and the lower surface of the chamber 122 is formed by the upper surface of the packing 126. Like the packings 112 and 118, the packing 126 has a substantially cylindrical lip portion 128. This lip portion 128 is in contact with the outer surface of the first pipe 92.

The packing 126 is fixed to the upper surface of a cylindrical member 130 inserted into the rotary shaft body 84 coaxially therewith through the rear end thereof (the lower end in FIG. 1). A chamber 132 is formed between the cylindrical member 130 and the lower surface of the packing 126. The cylindrical member 130 has a vertical infusion tube 134 along its axial centerline.

The opening at the end of the first pipe 92 is positioned inside the chamber 132, and the first pipe 92 and the vertical infusion tube 134 are connected by the chamber 132.

The transverse infusion tube 116 is connected to a vertical infusion tube 136 provided in parallel with the axial centerline of the rotary shaft body 84. A plug 138 is fitted in the opening of the transverse infusion tube 116 in the side of the rotary shaft body 84. The transverse infusion tube 124 is also connected to a vertical infusion tube 140 inside the rotary shaft body 84. A plug 142 is fitted in the opening of the transverse infusion tube 124.

With a first preferred embodiment of an animal infusion tube adaptor 80 so constructed, three medicinal liquids or the like supplied from the equipment side are sent into the pipe 90 in the fixed shaft body 82 and then through the vertical infusion tubes in the rotary shaft body 84 to the animal. At this time, in the adaptor 80, liquid pressure acts on the outer surfaces of the lip portions 110, 120 and 128 of the packings 112, 118 and 126 from the chambers 114, 122 and 132, the lip portions make strong contact with the pipes 96, 94 and 92 around which they are respectively fitted, and because the passages which the medicinal liquids pass through are thereby watertightly separated, and the liquids do not mix or leak out of the adaptor 80.

Because the fixed shaft body 82 connected to the equipment side and the rotary shaft body 84 connected to the animal side are connected by the two bearings 106 and 108, lateral oscillation of the rotary shaft body 84 is prevented. Also, at this time, because only the lip portions of the packings are fitted on the outside of the pipe 90 extending from the fixed shaft body 82 to inside the rotary shaft body 84, as described above, the rotary shaft body 84 is able to rotate extremely lightly.

Figure 3:
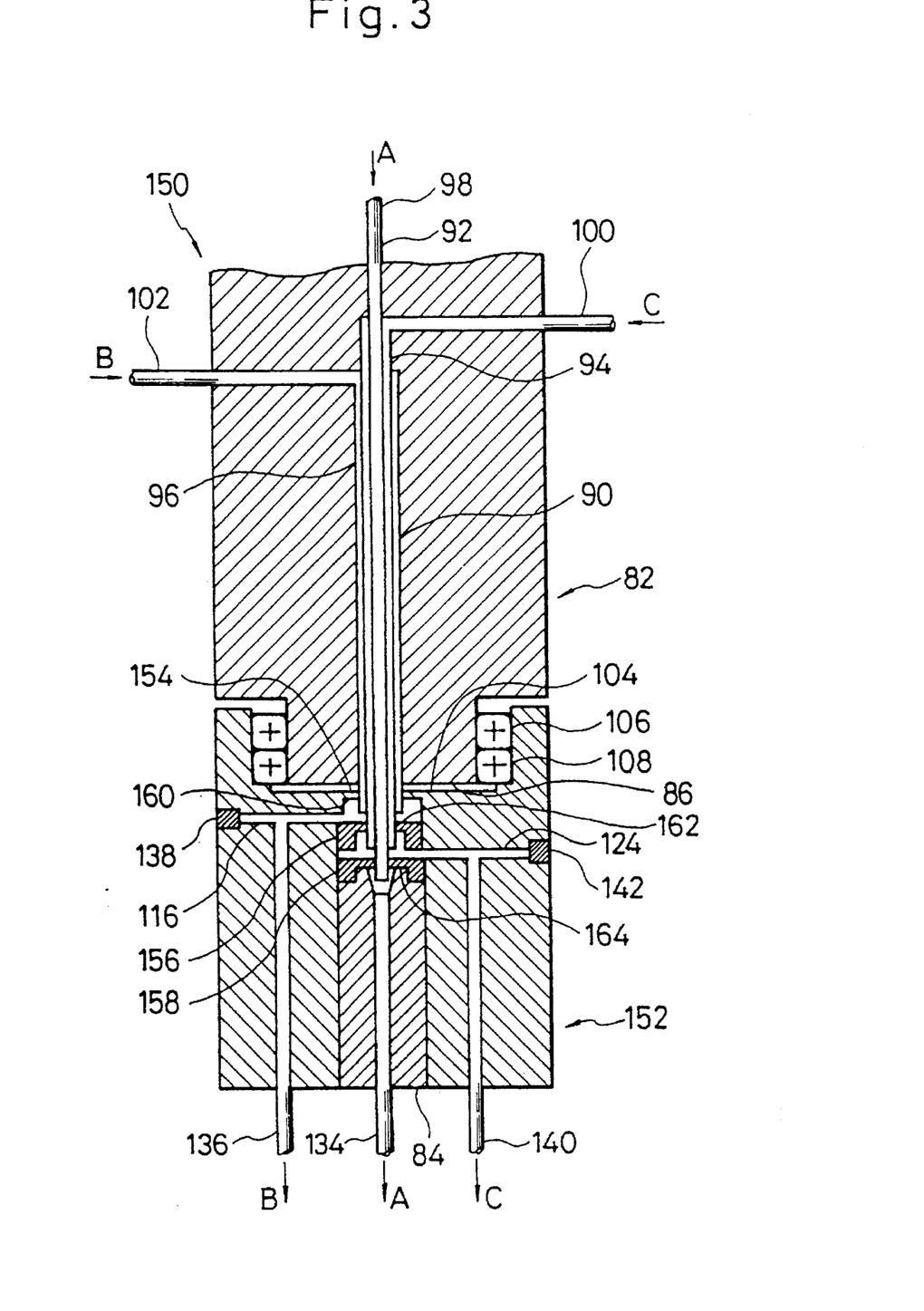
FIG. 3 is a sectional view of a second preferred embodiment of an animal infusion tube adaptor according to the invention.
Figure 4:
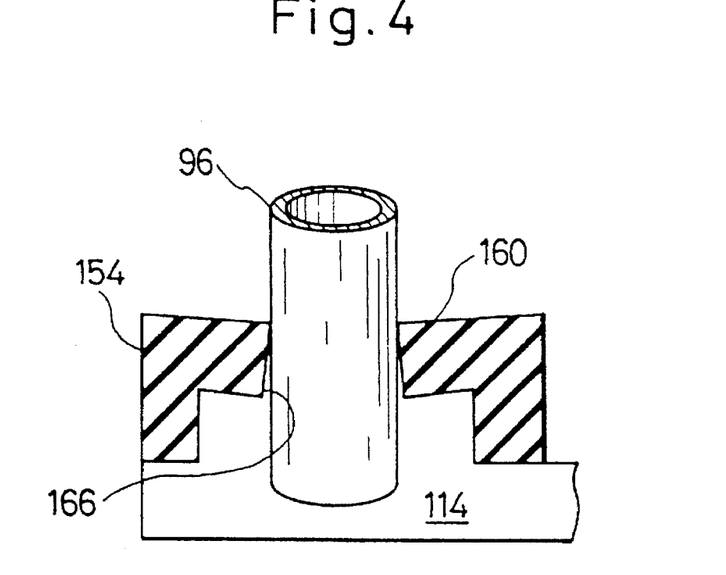
FIG. 4 is an enlarged detail sectional view of a packing used in the adaptor of FIG. 3.
Figure 5:
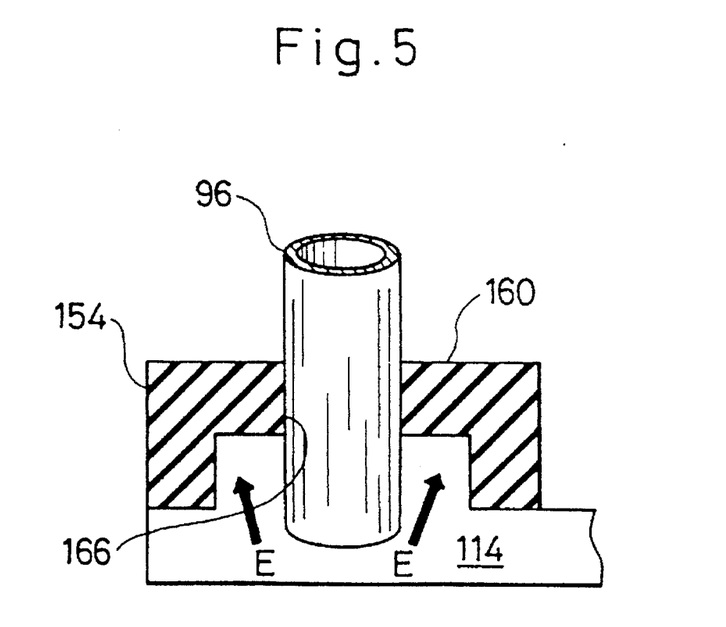
FIG. 5 is an enlarged detail sectional view showing deformation of a packing used in the adaptor of FIG. 3.

A second preferred embodiment of the invention will now be described with reference to FIGS. 3–5. FIG. 3 is a vertical sectional view of a second preferred embodiment of an animal infusion tube adaptor according to the invention. FIGS. 4 and 5 are schematic sectional views showing deformation of a packing shown in FIG. 3.

In this second preferred embodiment of an animal infusion tube adaptor 150, the shapes of lip portions of packings provided in a rotary shaft body 152 are different from the shapes of the lip portions of the packings in the first preferred embodiment described above. These packings 154, 156 and 158 and their respective lip portions 160, 162 and 164 are as a whole flat plate shaped and each has a pipe hole 166 which is tapered so that its diameter gradually decreases along one direction of the pipe axial centerline.

When liquid pressure is applied to the lower surface of the lip portion 160 by liquid flowing into the chamber 114, as shown in FIG. 5, the lip portion 160 is deformed and pushed upward by the liquid pressure (arrow E) and the whole of the inner surface of the pipe hole 166 makes contact with the outer surface of the pipe 96.

In the animal infusion tube adaptor 150 of this second preferred embodiment, because only the inner surfaces of the pipe holes in the lip portions 160, 162 and 164 make contact with the pipe 90 extending from the fixed shaftsbody 82 connected to the equipment side to the inside of the rotary shaft body 152 connected to the animal side, the rotary shaft body 152 is able to rotate extremely freely.

The rest of the constitution of this second preferred embodiment is the same as that of the first preferred embodiment described above; the same parts have been given the same reference numerals and a description thereof will be omitted.

Figure 6:
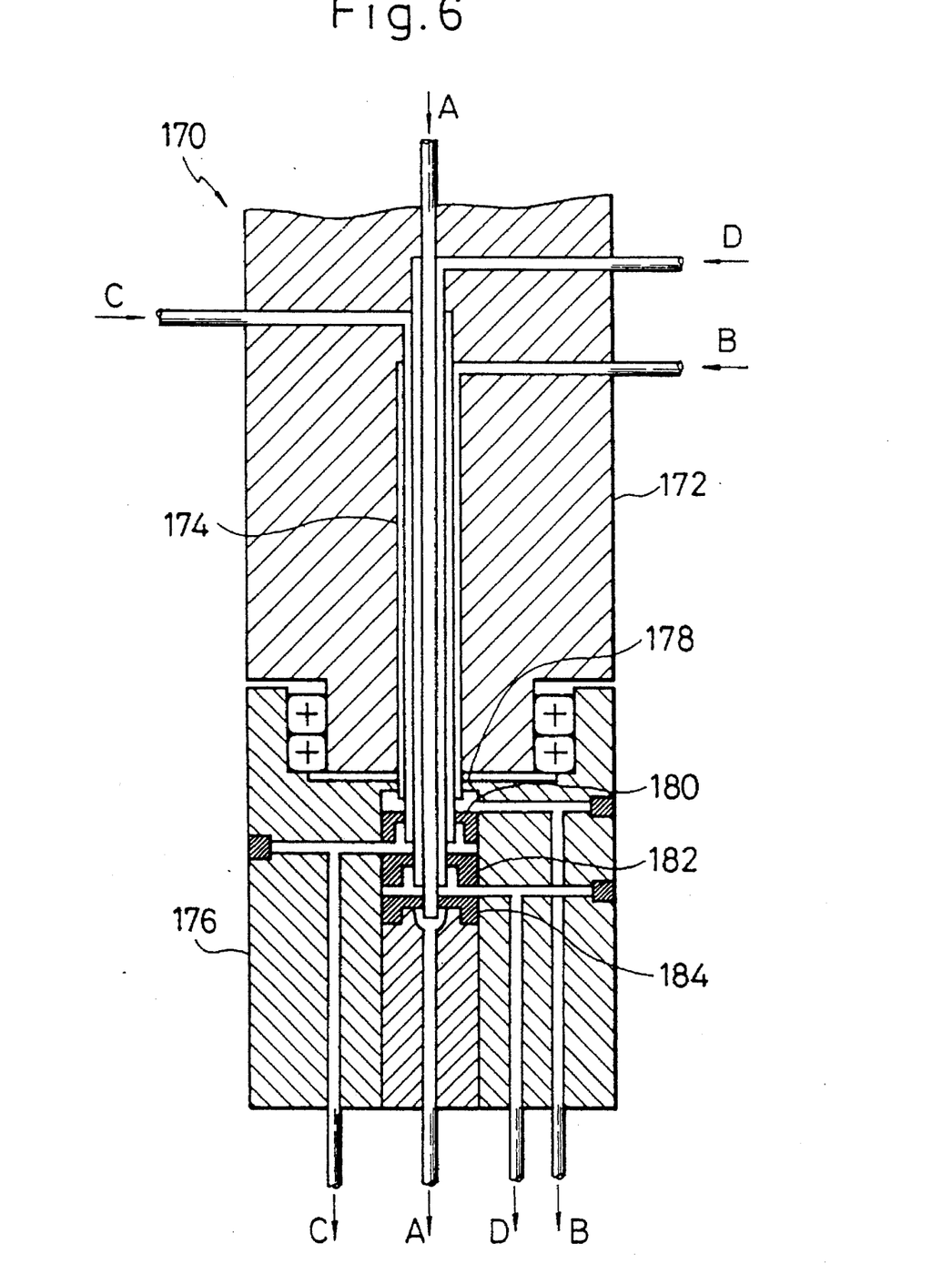
FIG. 6 is a sectional view of an animal infusion tube adaptor according to a third preferred embodiment of the invention.

A third preferred embodiment of the invention will now be described with reference to FIG. 6. An animal infusion tube adaptor 170 according to this third preferred embodiment has four pipes, one more pipe than the animal infusion tube adaptor 150 of the second preferred embodiment described above (which has three pipes), and can supply four different infusions. A coaxial quadruple pipe 174 is embedded in a fixed shaft body 172. The end of this quadruple pipe 174 passes into a rotary shaft body 176 rotatably attached to the fixed shaft body 172.

Inside the rotary shaft body 176, four packings 178, 180, 182 and 184 are provided for the four pipes of the quadruple pipe 174. Although not shown in the drawings, these packings have lip portions as same as those of the second preferred embodiment described above and have the same effects.

With this invention five or more pipes can be used and five or more infusions supplied.

As described above, in an animal infusion tube adaptor according to the invention,.because it is possible to keep down the sliding resistance between infusion pipes and sealing members, and the fixed shaft body and the rotary shaft body are connected by a plurality of bearings, the rotary shaft body can rotate extremely freely and the overall constitution is small. As a result, even with a small animal such as a mouse or a rat, it is possible to supply a plurality of infusions continuously while causing the animal almost no stress. Also, an adaptor according to the invention has a relatively simple constitution and can be applied to other uses such as blood pressure measurement and collection of body substances or taking of biological samples.

In an adaptor according to the invention, the higher the liquid pressure applied to the lip portions becomes, the more strongly the lip portions contract and make contact with the outer surfaces of the pipes and the better the sealing that is effected. Reversely, when the liquid pressure is low, the pressure pushing the lip portions onto the outer surfaces of the pipes is small and adequate sealing and low sliding resistance can be obtained.

What is claimed is:

1. An adaptor disposed midway along a plurality of tubes running between an animal and an equipment, comprising:

a first shaft body to which equipment side tubes are connected and having an end surface;

a second shaft body to which animal side tubes are connected and having an end surface;

a cylindrical projection provided at one end of one of the first and second shaft bodies;

a cylindrical first recess formed at one end of the other of the first and second shaft bodies, the projection being inserted into the first recess;

an annular bearing disposed between the projection and the first recess for rotatably joining the first shaft body and the second shaft body;

coaxial pipes extending from a central portion of one of the end surfaces of the first and second shaft bodies and being formed of at least inner and outer pipes, the coaxial pipes projecting from said one of the end surfaces such that the inner pipe located inside the outer pipe extends longer than the outer pipe from said one of the end surfaces;

a cylindrical second recess for receiving the coaxial pipes provided in a central portion of the other of the end surfaces of the first and second shaft bodies;

at least one seal member fitted around one of the inner and outer pipes, the seal member dividing the second recess in a shaft centerline direction into a plurality of chambers, the seal member making contact with an outer surface of said one of the inner and outer pipes and an inner surface of the second recess so that one of the chambers communicates with one of the inner and outer pipes;

liquid passages connecting the plurality of chambers to an outside of the first and second shaft bodies; and at least one lip portion provided around an inner edge of said at least one seal member, the lip portion being pushed into contact with said one of the inner and outer pipes around which the seal member is fitted by liquid pressure applied from said one of the inner and outer pipes.

2. An adaptor according to claim 1, wherein the lip portion is cylindrical.

3. An adaptor according to claim 1, wherein an inner surface of the lip portion which abuts with the outer surface of the one of the inner and outer pipes is tapered so that its diameter gradually decreases along the shaft centerline direction and the lip portion has such flexibility that it can be so deformed by liquid pressure applied in said direction that a whole area of the inner surface of the lip portion makes contact with the outer surface of the one of the inner and outer pipes.

4. An adaptor according to claim 1, wherein there are at least three chambers.

5. An adaptor according to claim 1, wherein a outer surface of the lip portion is tapered.

6. An adaptor according to claim 1, wherein the coaxial pipes are formed of the inner pipe, at least one intermediate pipe located coaxially outside the inner pipe, and the outer pipe located coaxially outside the intermediate pipe, one of the seal members being fitted around the inner pipe, the intermediate pipe and the outer pipe, respectively, to thereby define the chambers inside the seal members.

7. An adaptor according to claim 1, wherein the first shaft body is a fixed body immovable connected to the equipment side tubes, and the second shaft body is a rotary shaft body.

* * * * *